United States Patent
Kanan et al.

(10) Patent No.: US 12,424,321 B2
(45) Date of Patent: Sep. 23, 2025

(54) SYSTEMS AND METHODS TO PROCESS ELECTRONIC IMAGES TO PREDICT BIALLELIC MUTATIONS

(71) Applicant: PAIGE.AI, Inc., New York, NY (US)

(72) Inventors: Christopher Kanan, Pittsford, NY (US); Jorge S. Reis-Filho, New York, NY (US)

(73) Assignee: Paige.AI, Inc., New York, NY (US)

( * ) Notice: Subject to any disclaimer, the term of this patent is extended or adjusted under 35 U.S.C. 154(b) by 602 days.

(21) Appl. No.: 17/811,090

(22) Filed: Jul. 7, 2022

(65) Prior Publication Data

US 2023/0008197 A1    Jan. 12, 2023

Related U.S. Application Data

(60) Provisional application No. 63/219,668, filed on Jul. 8, 2021.

(51) Int. Cl.
*G16H 50/20* (2018.01)
*G16H 30/20* (2018.01)

(52) U.S. Cl.
CPC ............ *G16H 50/20* (2018.01); *G16H 30/20* (2018.01)

(58) Field of Classification Search
None
See application file for complete search history.

(56) References Cited

U.S. PATENT DOCUMENTS

2020/0364587 A1 * 11/2020 Kapur ................... G16H 30/40

OTHER PUBLICATIONS

Harrison Beth T et al: "Genomic profiling of pleomorphic and florid lobular carcinoma in situ reveals highly recurrent ERBB2 and ERBB3 alterations", Modern Pathology, Nature Publishing Group, GB, vol. 33, No. 7, Jan. 13, 2020, pp. 1287-1297 (Year: 2020).*
Harrison Beth T et al: "Genomic profiling of pleomorphic and florid lobular carcinoma in situ reveals highly recurrent ERBB2 and ERBB3 alterations", Modern Pathology, Nature Publishing Group, GB, vol. 33, No. 7, Jan. 13, 2020, pp. 1287-1297 (Year: 2020) (Year: 2020).*
Harrison Beth T et al: "Genomic profiling of pleomorphic and florid lobular carcinoma in situ reveals highly recurrent ERBB2 and ERBB3 alterations", Modern Pathology, Nature Publishing Group, GB, vol. 33, No. 7, Jan. 13, 2020, pp. 1287-1297.
Geiersbach Katherine B et al: "Current concepts in breast cancer genomics: An evidence based review by the CGC breast cancer working group", Cancer Genetics, Elsevier, Amsterdam, Nl, vol. 244, Feb. 8, 2020, pp. 11-20.

* cited by examiner

*Primary Examiner* — Andrew H Lam
(74) *Attorney, Agent, or Firm* — Bookoff McAndrews, PLLC

(57) ABSTRACT

A computer-implemented method may diagnose invasive lobular carcinoma. The method may include receiving one or more digital images into a digital storage device, applying a trained machine learning module to detect a presence or absence of CDH1 biallelic genetic inactivation and/or CDH1 biallelic mutation from the received one or more digital images, and determining whether the patient has invasive lobular carcinoma using the detected presence or absence of the CDH1 biallelic genetic inactivation and/or CDH1 biallelic mutation as ground truth. The one or more digital images may include images of breast tissue of a patient.

14 Claims, 6 Drawing Sheets

SYSTEMS AND METHODS TO PROCESS ELECTRONIC IMAGES TO PREDICT BIALLELIC MUTATIONS

RELATED APPLICATION(S)

This application claims priority to U.S. Provisional Application No. 63/219,668 filed Jul. 8, 2021, the entire disclosure of which is hereby incorporated herein by reference in its entirety.

FIELD OF THE DISCLOSURE

Various embodiments of the present disclosure pertain generally to image processing methods. More specifically, particular embodiments of the present disclosure relate to systems and methods for predicting biallelic mutations in whole slide images of histology specimens.

BACKGROUND

Invasive lobular carcinoma (ILC) is the most frequent special histologic subtype of breast cancer (BC). ILC may be identifiable by pathologic assessment given its distinctive discohesive growth pattern, largely caused by the CDH1 gene inactivation. In breast cancer, over 95% of CDH1 biallelic inactivation is found in ILCs. Compared to common forms of breast cancer, ILCs may display lower response to chemotherapy and selective estrogen receptor modulators. A low inter-observer agreement for a diagnosis of ILC, however, may render an inclusion of histologic subtyping in therapeutic decision making challenging. Artificial intelligence (AI)-based algorithms may improve pathologic diagnosis, but their performance may depend on the ground truth labeling used.

The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for diagnosing a disease such as invasive lobular carcinoma.

A computer-implemented method may diagnose invasive lobular carcinoma. The method may include receiving one or more digital images into a digital storage device, applying a trained machine learning module to detect a presence or absence of CDH1 biallelic genetic inactivation and/or CDH1 biallelic mutation from the received one or more digital images, and determining whether the patient has invasive lobular carcinoma using the detected presence or absence of the CDH1 biallelic genetic inactivation and/or CDH1 biallelic mutation as ground truth. The one or more digital images may include images of breast tissue of a patient. The trained machine learning module may have been trained using a plurality of digital images of breast tissue from a plurality of patients and associated mutation data. The associated mutation data may include integrated mutation profiling of actionable cancer targets (MSK-IMPACT) targeted sequencing data. The trained machine learning module may have been trained using a 10-fold cross-validation method. The method may include applying the trained machine learning module to predict a lobular phenotype.

The method may include receiving supplemental patient information. Determining whether the patient has invasive lobular carcinoma may be based on the received supplemental patient information.

The supplemental patient information may include patient demographics, medical history, cancer treatment history, family history, past biopsy or cytology information, additional test results, radiology imaging, genomic test results, molecular test results, historical pathology specimen images, and/or location of the breast tissue. The method may include outputting the determination on an electronic display.

A system may diagnose invasive lobular carcinoma. The system may include at least one memory storing instructions and at least one processor configured to execute the instructions to perform operations. The operations may include receiving one or more digital images into a digital storage device, applying a trained machine learning module to detect a presence or absence of CDH1 biallelic genetic inactivation and/or CDH1 biallelic mutation from the received one or more digital images, and determining whether the patient has invasive lobular carcinoma using the detected presence or absence of the CDH1 biallelic genetic inactivation and/or CDH1 biallelic mutation as ground truth. The one or more digital images may include images of breast tissue of a patient. The method may include applying a trained machine learning module to detect a presence or absence of CDH1 biallelic genetic inactivation and/or CDH1 biallelic mutation from the received one or more digital images, and determining whether the patient has invasive lobular carcinoma using the detected presence or absence of the CDH1 biallelic genetic inactivation and/or CDH1 biallelic mutation as ground truth.

The trained machine learning module may have been trained using a plurality of digital images of breast tissue from a plurality of patients and associated mutation data. The associated mutation data may include integrated mutation profiling of actionable cancer targets (MSK-IMPACT) targeted sequencing data.

The trained machine learning module was trained using a 10-fold cross-validation method. The operations may comprise applying the trained machine learning module to predict a lobular phenotype.

The operations may comprise receiving supplemental patient information. Determining whether the patient has invasive lobular carcinoma may be based on the received supplemental patient information.

The supplemental patient information may include patient demographics, medical history, cancer treatment history, family history, past biopsy or cytology information, additional test results, radiology imaging, genomic test results, molecular test results, historical pathology specimen images, and/or location of the breast tissue. The operations may include outputting the determination on an electronic display.

A non-transitory computer-readable medium may store instructions that, when executed by a processor, cause the processor to perform operations for diagnosing invasive lobular carcinoma. The operations may include receiving one or more digital images into a digital storage device, the one or more digital images including images of breast tissue of a patient, applying a trained machine learning module to detect a presence or absence of CDH1 biallelic genetic inactivation and/or CDH1 biallelic mutation from the received one or more digital images, and determining whether the patient has invasive lobular carcinoma using the detected presence or absence of the CDH1 biallelic genetic inactivation and/or CDH1 biallelic mutation as ground truth.

The trained machine learning module may have been trained using a plurality of digital images of breast tissue from a plurality of patients and associated mutation data. The associated mutation data may include integrated mutation profiling of actionable cancer targets (MSK-IMPACT) targeted sequencing data.

The operations may include receiving supplemental patient information. Determining whether the patient has invasive lobular carcinoma may be based on the received supplemental patient information.

BRIEF DESCRIPTIONS OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Figure 1A:
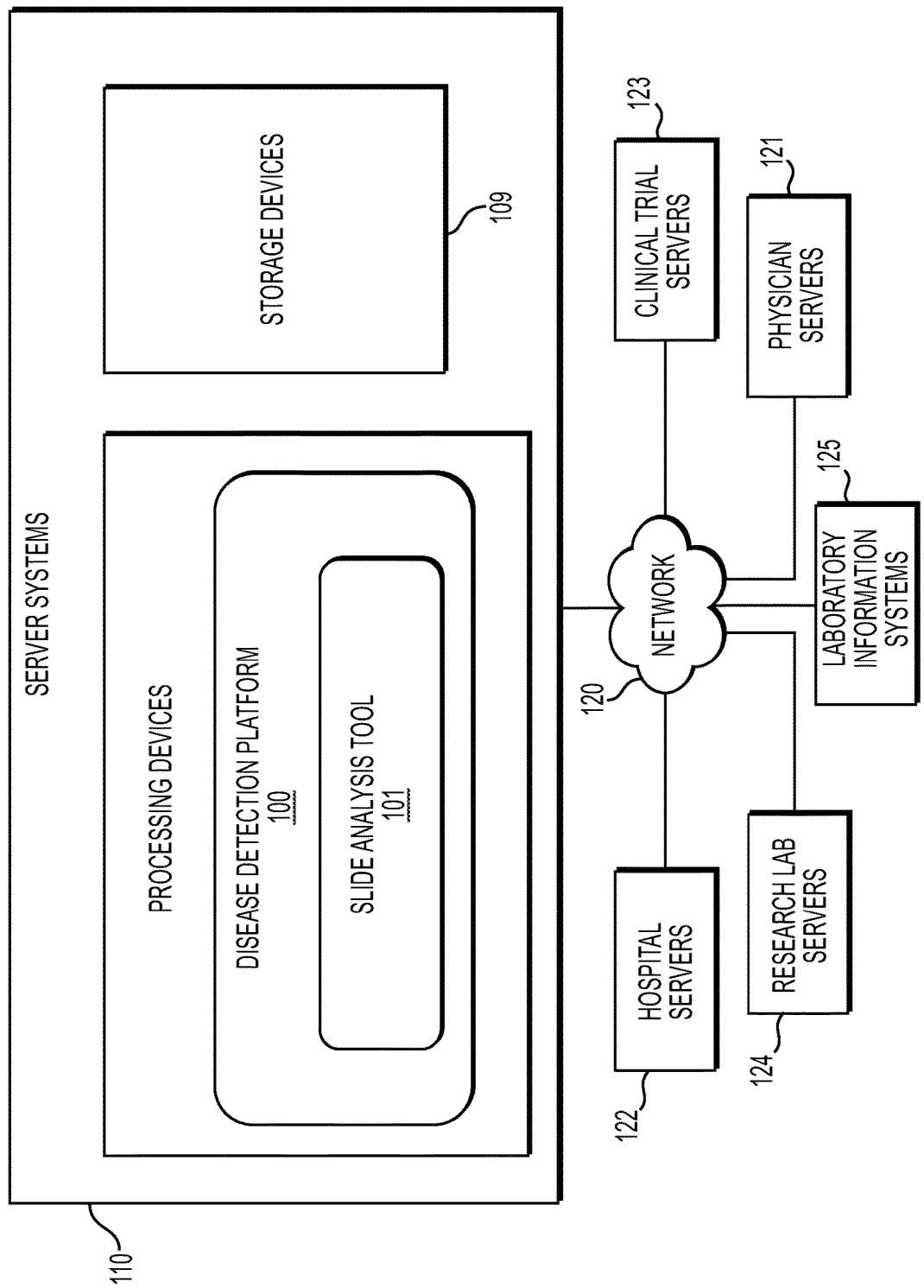
FIG. 1A illustrates an exemplary block diagram of a system and network to identify CDH1 biallelic mutations from digital or electronic slide images according to an exemplary embodiment of the present disclosure.

It is to be understood that both the foregoing general description and the following detailed description are exemplary and explanatory only and are not restrictive of the disclosed embodiments, as claimed.

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

Techniques presented herein describe an AI-based method for detection of lobular carcinoma using CDH1 biallelic mutations as ground truth. As used herein, ground truth may be information that is known to be true, provided by direct observation and/or measurement rather than inference. CDH1 biallelic mutations may be thought of us a mutation plus a loss-of-heterozygosity of a wild-type allele or two pathogenic somatic mutations.

By training a machine learning system to detect CDH1 biallelic mutations as ground truth rather than performing a histologic diagnosis of lobular carcinoma, which might be confounded by human subjectivity, an AI-based system may detect ILCs accurately, providing a new paradigm for the development of AI-based cancer classification systems.

Figure 1B:
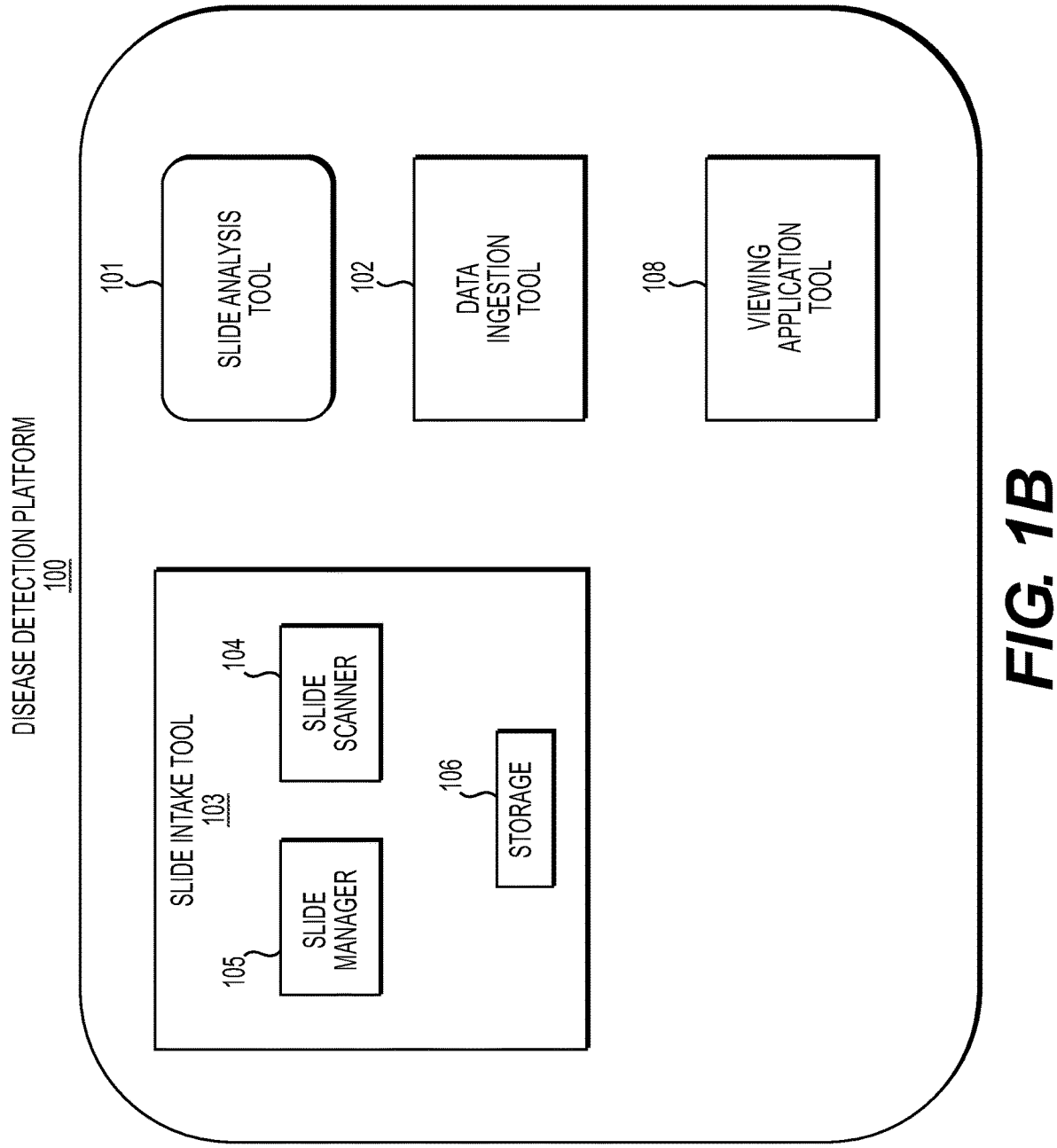
FIG. 1B illustrates an exemplary block diagram of a disease detection platform, according to an exemplary embodiment of the present disclosure.
Figure 1C:
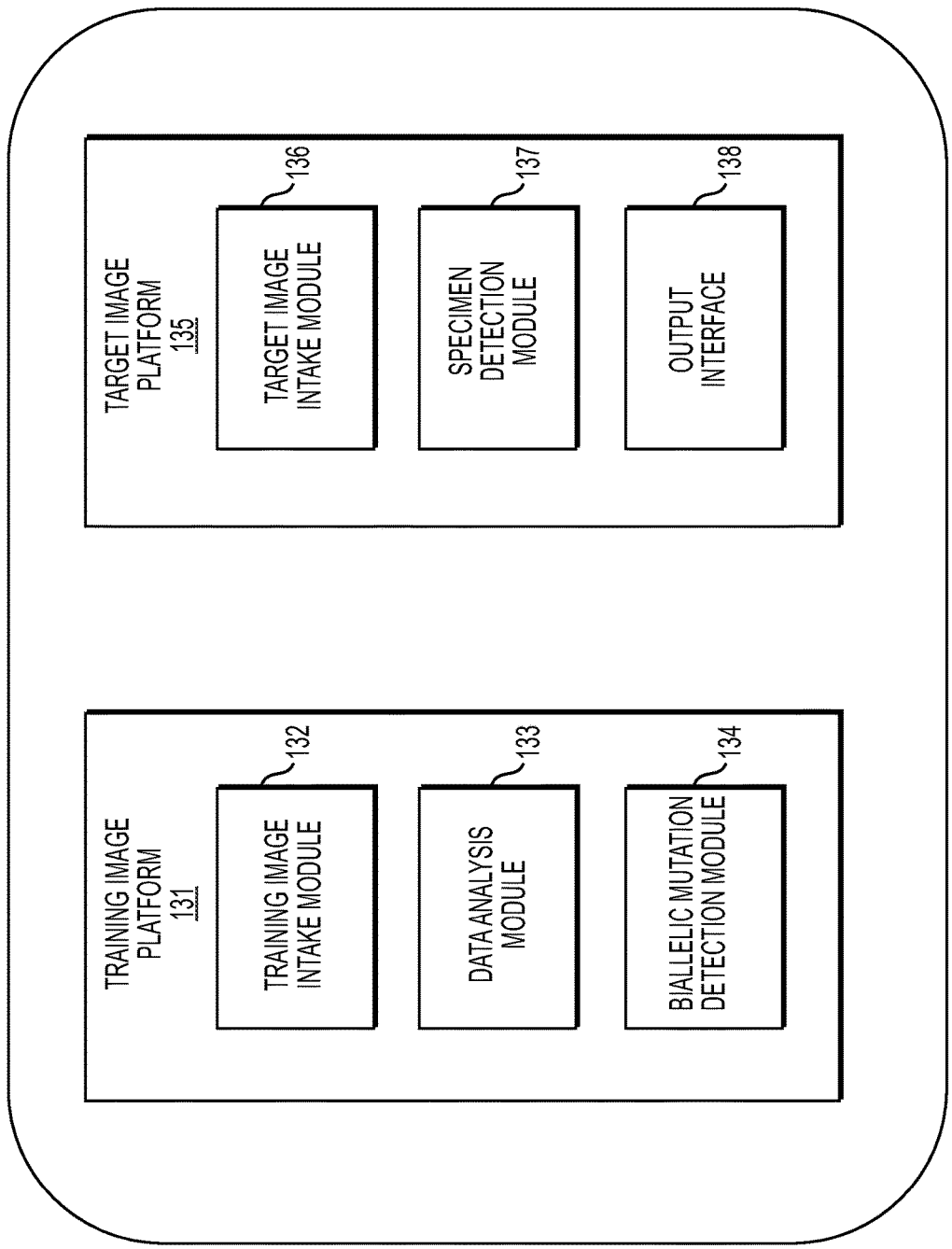
FIG. 1C illustrates an exemplary block diagram of a slide analysis tool, according to an exemplary embodiment of the present disclosure.

FIGS. 1A through 1C show a system and network to identify CDH1 biallelic mutations and/or diagnose a disease (e.g., Invasive lobular carcinoma (ILC) or breast cancer (BC)) from electronic or digital slide images according to an exemplary embodiment of the present disclosure.

Specifically, FIG. 1A illustrates an electronic network 120 that may be connected to servers at hospitals, laboratories, and/or doctor's offices, etc. For example, physician servers 121, hospital servers 122, clinical trial servers 123, research lab servers 124, and/or laboratory information systems 125, etc., may each be connected to an electronic network 120, such as the Internet, through one or more computers, servers and/or handheld mobile devices. According to an exemplary embodiment of the present application, the electronic network 120 may also be connected to server systems 110, which may include processing devices that are configured to implement a disease detection platform 100, which includes a slide analysis tool 101 for determining specimen property or image property information pertaining to digital pathology image(s), and using machine learning to determine whether a disease or infectious agent is present, according to an exemplary embodiment of the present disclosure. The slide analysis tool 101 may allow for rapid evaluation of 'adequacy' in liquid-based tumor preparations, facilitate the diagnosis of liquid based tumor preparations (cytology, hematology/hematopathology), and predict molecular findings most likely to be found in various tumors detected by liquid-based preparations. The slide analysis tool 101 may be configured to detect CDH1 biallelic mutations, and the disease detection platform 100 may use detected CDH1 biallelic mutations as ground truth to diagnose diseases, such as ILC or BC.

The physician servers 121, hospital servers 122, clinical trial servers 123, research lab servers 124 and/or laboratory information systems 125 may create or otherwise obtain images of one or more patients' cytology specimen(s), histopathology specimen(s), slide(s) of the cytology specimen(s), digitized images of the slide(s) of the histopathology specimen(s), or any combination thereof. The physician servers 121, hospital servers 122, clinical trial servers 123, research lab servers 124 and/or laboratory information systems 125 may also obtain any combination of patient-specific information, such as age, medical history, cancer treatment history, family history, past biopsy or cytology information, etc. The physician servers 121, hospital servers 122, clinical trial servers 123, research lab servers 124 and/or laboratory information systems 125 may transmit digitized slide images and/or patient-specific information to server systems 110 over the electronic network 120. Server system(s) 110 may include one or more storage devices 109 for storing images and data received from at least one of the physician servers 121, hospital servers 122, clinical trial servers 123, research lab servers 124, and/or laboratory information systems 125. Server systems 110 may also include processing devices for processing images and data stored in the storage devices 109. Server systems 110 may further include one or more machine learning tool(s) or capabilities. For example, the processing devices may include a machine learning tool for a disease detection platform 100, according to one embodiment. Alternatively or in addition, the present disclosure (or portions of the system and methods of the present disclosure) may be performed on a local processing device (e.g., a laptop).

The physician servers 121, hospital servers 122, clinical trial servers 123, research lab servers 124 and/or laboratory information systems 125 refer to systems used by pathologists for reviewing the images of the slides. In hospital settings, tissue type information may be stored in a laboratory information system 125.

FIG. 1B illustrates an exemplary block diagram of a disease detection platform 100 for determining specimen property or image property information pertaining to digital pathology image(s) using machine learning. The disease detection platform 100 may include a slide analysis tool 101, a data ingestion tool 102, a slide intake tool 103, a slide scanner 104, a slide manager 105, a storage 106, a laboratory information system 107, and a viewing application tool 108.

The slide analysis tool 101, as described below, refers to a process and system for determining data variable property or health variable property information pertaining to digital pathology image(s). Machine learning may be used to classify an image, according to an exemplary embodiment. The slide analysis tool 101 may also predict future relationships, as described in the embodiments below.

The data ingestion tool 102 may facilitate a transfer of the digital pathology images to the various tools, modules, components, and devices that are used for classifying and processing the digital pathology images, according to an exemplary embodiment.

The slide intake tool 103 may scan pathology images and convert them into a digital form, according to an exemplary embodiment. The slides may be scanned with slide scanner 104, and the slide manager 105 may process the images on the slides into digitized pathology images and store the digitized images in storage 106.

The viewing application tool 108 may provide a user with a specimen property or image property information pertaining to digital pathology image(s), according to an exemplary embodiment. The information may be provided through various output interfaces (e.g., a screen, a monitor, a storage device and/or a web browser, etc.).

The slide analysis tool 101, and one or more of its components, may transmit and/or receive digitized slide images and/or patient information to server systems 110, physician servers 121, hospital servers 122, clinical trial servers 123, research lab servers 124, and/or laboratory information systems 125 over a network 120. Further, server systems 110 may include storage devices for storing images and data received from at least one of the slide analysis tool 101, the data ingestion tool 102, the slide intake tool 103, the slide scanner 104, the slide manager 105, and viewing application tool 108. Server systems 110 may also include processing devices for processing images and data stored in the storage devices. Server systems 110 may further include one or more machine learning tool(s) or capabilities, e.g., due to the processing devices. Alternatively, or in addition, the present disclosure (or portions of the system and methods of the present disclosure) may be performed on a local processing device (e.g., a laptop).

Any of the above devices, tools, and modules may be located on a device that may be connected to an electronic network such as the Internet or a cloud service provider, through one or more computers, servers and/or handheld mobile devices.

FIG. 1C illustrates an exemplary block diagram of a slide analysis tool 101, according to an exemplary embodiment of the present disclosure. The slide analysis tool 101 may include a training image platform 131 and/or a target image platform 135.

According to one embodiment, the training image platform 131 may include a training image intake module 132, a data analysis module 133, and a biallelic mutation detection module 134.

The training data platform 131, according to one embodiment, may create or receive training images that are used to train a machine learning model to effectively analyze and classify digital pathology images and/or analyze or detect features within the digital pathology images. For example, the training images may be received from any one or any combination of the server systems 110, physician servers 121, hospital servers 122, clinical trial servers 123, research lab servers 124, and/or laboratory information systems 125. Images used for training may come from real sources (e.g., humans, animals, etc.) or may come from synthetic sources (e.g., graphics rendering engines, 3D models, etc.). Examples of digital pathology images may include (a) digitized slides stained with a variety of stains, such as (but not limited to) H&E, Hematoxylin alone, IHC, molecular pathology, etc.; and/or (b) digitized tissue samples from a 3D imaging device, such as microCT.

The training image intake module 132 may create or receive a dataset comprising one or more training datasets corresponding to one or more health variables and/or one or more data variables. For example, the training datasets may be received from any one or any combination of the server systems 110, physician servers 121, hospital servers 122, clinical trial servers 123, research lab servers 124, and/or laboratory information systems 125. This dataset may be kept on a digital storage device.

The data analysis module 133 may identify whether an area belongs to a region of interest or salient region, such as regions containing biallelic mutations, or to a background of a digitized image. The biallelic mutation detection module 134 may analyze digitized images and determine whether the region contains one or more biallelic mutations. The identification of such may trigger an alert to a user and/or an indication that further analysis is required.

According to one embodiment, the target image platform 135 may include a target image intake module 136, a specimen detection module 137, and an output interface 138. The target image platform 135 may receive a target image and apply the machine learning model to the received target image to determine a characteristic of a target data set. For example, the target data may be received from any one or any combination of the server systems 110, physician servers 121, hospital servers 122, clinical trial servers 123, research lab servers 124, and/or laboratory information systems 125. The target image intake module 136 may receive a target dataset corresponding to a target health variable or a data variable.

The specimen detection module 137 may apply the machine learning model to the target dataset to determine a characteristic of the target health variable or a data variable. For example, the specimen detection module 137 may detect a trend of the target relationship. The specimen detection module 137 may also apply the machine learning model to the target dataset to determine a quality score for the target dataset. Further, the specimen detection module 137 may apply the machine learning model to the target images to determine whether a target element is present in a determined relationship.

The output interface 138 may be used to output information about the target data and the determined relationship (e.g., to a screen, monitor, storage device, web browser, etc.). The output interface 138 may display identified salient regions of analyzed slides according to a policy or strategy (e.g., by zooming, panning, and/or jumping) to navigate the slides. The final result or output on the output interface 138 may appear as an automated, customized video or "tour" of the slides.

Using the disease detection platform 100, a convolutional neural network (CNN) may be developed to detect or predict CDH1 biallelic genetic inactivation (AI-CDH1) using whole slide images (WSI) of primary breast cancers (BCs) with available integrated mutation profiling of actionable cancer targets (MSK-IMPACT) targeted sequencing data. The model may be trained using a 10-fold cross-validation method to detect biallelic mutations.

The mean number of positive and negative samples in a training set may range from 85.2 (SD=2.57) to 562.8 (SD=10.51) per fold, respectively. The evaluation set may consist of a mean of 14.2 (SD=2.04) positive and 93.8 (SD=9.13) negative samples. The performance of an AI-CDH1 classifier (e.g., implemented as slide analysis tool 101) may be evaluated to predict the lobular phenotype and CDH1 status using original and revised labels, following a histopathologic re-review of the histologic type and CDH1 status curation. The latter method may be conducted by incorporating information on biallelic CDH1 inactivation beyond CDH1 mutations (homozygous deletions, deleterious structural rearrangements, and loss-of-heterozygosity and gene promoter methylation).

When the mean number of positive and negative samples in the training set and the evaluation set have the above ranges, the AI-CDH1 classifier may predict biallelic CDH1 mutations with an area under the curve (AUC)=0.944 (95 CI:0.925-0.963), sensitivity=91.6% and specificity=85.9%, PPV=49.8%, NPV=98.5% and accuracy=86.7%, and the original 'lobular phenotype' with an AUC=0.941 (95 CI: 0.922-0.960), sensitivity=89%, specificity=86.7%, PPV=55.6%, NPV=97.7% and accuracy=87.1%. Review of the CDH1 gene status may reveal that less than 1% (e.g., 0.7% or 7/957) of BCs lacking CDH1 biallelic mutations harbor biallelic CDH1 inactivation by promoter methylation, homozygous deletions or structural rearrangements. The AI-CDH1 classifier may detect all seven reclassified BCs, and predict the revised CDH1 biallelic inactivation with an AUC=0.948 (95 CI: 0.930-0.966), sensitivity=92%, specificity=86.5%, PPV=52.3%, NPV=98.5% and accuracy=87.2%. Upon histologic re-review, which may result in reclassification of less than 4% (e.g., 3.9% or 36/927) non-lobular BCs as 'lobular' and less than 3% (e.g., 2.9% or 5/173) 'lobular' BCs as 'non-lobular', the AI-CDH1 classifier may detect the 'lobular phenotype' with an AUC=0.953 (95 CI: 0.935-0.971), sensitivity=90.7%, specificity=89.7%, PPV=66.8%, NPV=97.7% and accuracy=89.9%. Using the revised histologic re-classification and CDH1 biallelic inactivation status labels, the AI-CDH1 classifier may predict the lobular phenotype irrespective of CDH1 status (P>0.05).

Figure 2:
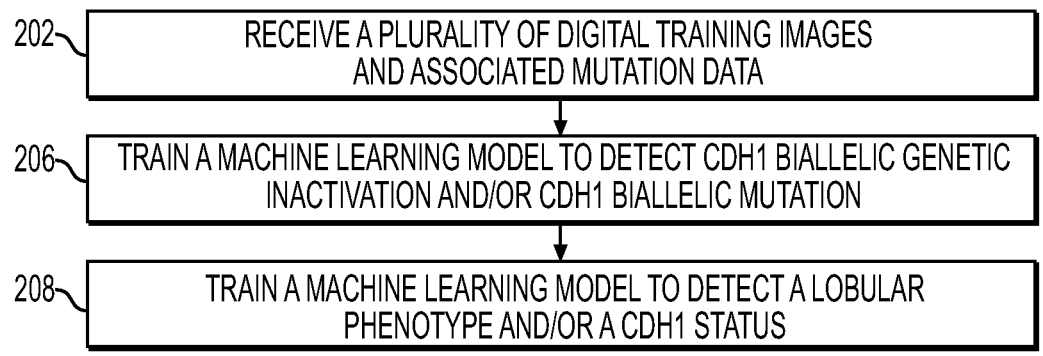
FIG. 2 is a flowchart illustrating an exemplary method of training a machine learning module to detect or predict CDH1 biallelic genetic inactivation and/or CDH1 biallelic mutation according to an exemplary embodiment.

Referring to FIG. 2, a method 200 of training an AI-CDH1 classification module may include the following steps. The method 200 may include a step 202 of receiving a plurality of digital or electronic training images (e.g., whole slide images (WSIs)) of a medical specimen (biopsy, histology, CT, MRI, etc.) into a digital storage device (e.g., hard drive, network drive, cloud storage, RAM, etc.) with associated mutation data.

The medical specimen may include breast tissue. The plurality of digital training images may derive from a plurality of medical specimens from a plurality of patients.

The associated mutation data may correspond to each image and/or each patient of the plurality of patients. The mutation data may include an indication of a presence or absence of CDH1 biallelic genetic inactivation (AI-CDH1) and/or a CDH1 biallelic mutation. The mutation data may include MSK-IMPACT targeted sequencing data. The mutation data may also include information on biallelic CDH1 inactivation beyond CDH1 mutations, such as information relating to homozygous deletions, deleterious structural rearrangements, and loss-of-heterozygosity and gene promoter methylation.

In some examples, the plurality of digital training images may include images of medical specimen that are not known to have cancer or breast cancer. In other examples, all of the plurality of digital training images may be of medical specimen known to have cancer or a particular type of cancer (e.g., breast cancer), but only some may be known to have invasive lobular carcinoma (ILC), CDH1 biallelic mutations, and/or CDH1 biallelic genetic inactivation (AI-CDH1). In some examples, over a thousand (e.g., 1,100) digital images indicating primary BC with available MSK-IMPACT targeted sequencing data may be used.

The method 200 may include a step 206 of training a machine learning model (e.g., a convolutional neural network (CNN)) that receives, as input, the plurality of training images to detect or predict CDH1 biallelic genetic inactivation and/or CDH1 biallelic mutation. The method 200 may use, for example, a 10-fold cross-validation method where the training images are divided into ten (10) groups. Nine groups may be used for training while one group may be reserved for testing. Step 206 may be repeated ten times, each time reserving a different one of the ten groups for testing.

Additionally or alternatively, a labeling and/or supervision method (e.g., weak supervision) that implements multiple instance learning (MIL) using labeling (e.g., weak labeling) of the digital image or a collection of images. Alternatively or in addition thereto, bounding box supervision, polygon-based supervision, pixel-level labelling, voxel-level labeling, and/or semantic or instance segmentation may be used.

Detecting CDH1 biallelic genetic inactivation and/or CDH1 biallelic mutation may include detecting or predicting a mutation and a loss-of-heterozygosity of a wild-type allele or two pathogenic somatic mutations. Labels may correspond to the presence or absence of AI-CDH1, the presence or absence of the CDH1 biallelic mutation, the presence or absence of the loss-of-heterozygosity of a wild-type allele, and/or the presence or absence of a pathogenic somatic mutation. The detected CDH1 biallelic genetic inactivation and/or CDH1 biallelic mutation may be used as ground truth in diagnosing a disease such as invasive lobular carcinoma and/or breast cancer.

The method 200 may include a step 208 of training the machine learning model to predict a lobular phenotype and/or a CDH1 status using original and/or revised labels, and/or based on the detected CDH1 biallelic genetic inactivation and/or CDH1 biallelic mutation.

For example, the method 200 may include training the machine learning model, in step 208, to predict a lobular phenotype and/or a CDH1 status using original labels and/or based on the detected CDH1 biallelic genetic inactivation and/or CDH1 biallelic mutation. The method 200 may further include performing a histopathologic re-review of a histologic type and CDH1 status curation by incorporating information on biallelic CDH1 inactivation beyond CDH1 mutations, such as homozygous deletions, deleterious structural rearrangements, and loss-of-heterozygosity and gene promoter methylation, and, after performing the histopathologic re-review, the method 200 may include repeating steps 206 and/or 208 using revised labels.

Figure 3:
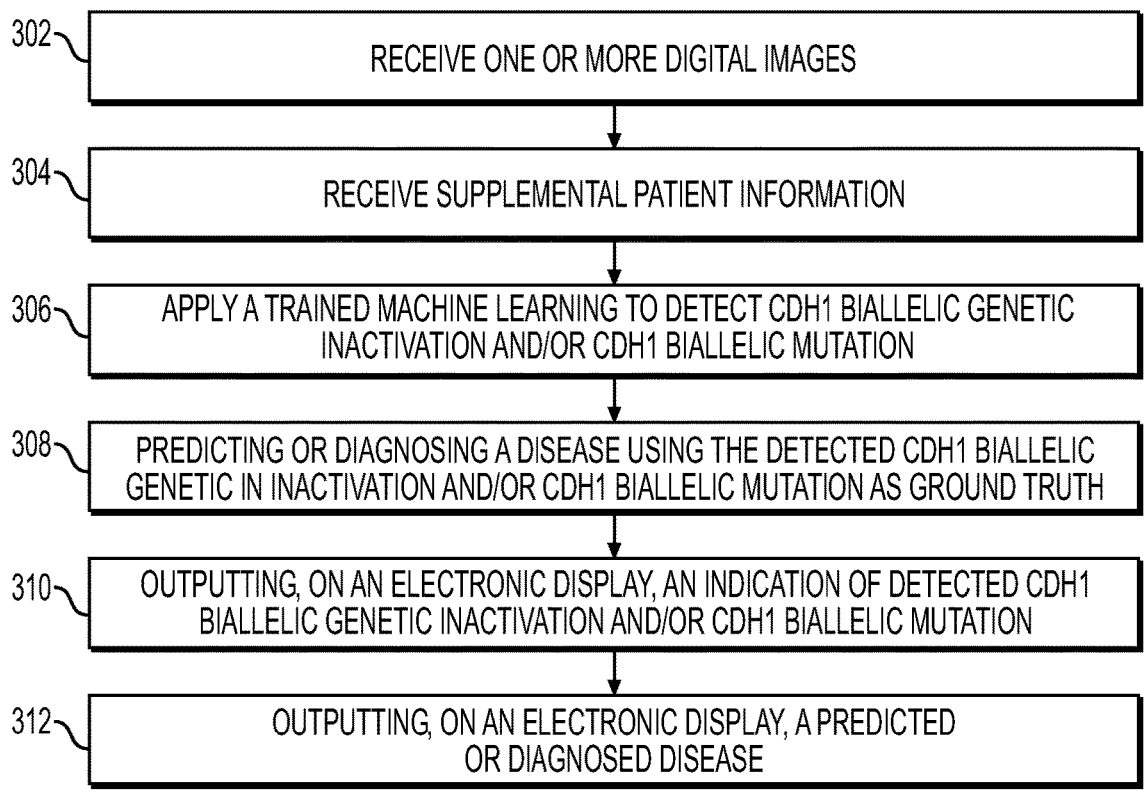
FIG. 3 is a flowchart illustrating an exemplary method of using a machine learning module that detects or predicts CDH1 biallelic genetic inactivation and/or CDH1 biallelic mutation according to an exemplary embodiment.

Referring to FIG. 3, a method 300 of using a trained machine learning system (e.g., a trained AI-CDH1 classification module) to diagnose a disease based on CDH1 biallelic mutation and/or AI-CDH1 may include the following steps. The method 302 may include a step of receiving one or more digital or electronic images (e.g., WSIs) of an instant medical sample to be analyzed (e.g., a patient suspected of having breast cancer and/or invasive lobular carcinoma) for storage at a digital storage device (e.g., hard drive, network drive, cloud storage, RAM, etc.). The images may depict slides, which may be unstained or stained with one or more stains (e.g., H&E, IHC, FISH, CISH, special stains, etc.). The instant medical sample may include a biopsy or tissue sample such as of breast tissue.

The method 300 may include a step 304 of receiving supplemental patient information. The supplemental patient information may include patient demographics (e.g., age, gender), medical history, cancer treatment history, family history, past biopsy or cytology information, additional test results, radiology imaging, genomic test results, molecular test results, historical pathology specimen images, information about the specimen (e.g., location of specimen sample, position in block, etc.) etc. The received supplemental patient information may be transformed into a vector representation and integrated with and/or concatenated into a neural network of the machine learning model.

The method 300 may include a step 306 of applying a trained machine learning module (e.g., the AI-CDH1 classification module referred to with reference to FIG. 2) to detect or predict CDH1 biallelic genetic inactivation and/or CDH1 biallelic mutation in the received one or more digital images.

The method 300 may further include a step 308 of predicting or diagnosing a disease (e.g., cancer, breast cancer, invasive lobular carcinoma, and/or a lobular phenotype) using the detected CDH1 biallelic genetic inactivation and/or CDH1 biallelic mutation as ground truth. For example, step 308 of predicting or diagnosing a disease may include determining a presence of CDH1 biallelic genetic inactivation (e.g., based on a detected CDH1 biallelic mutation), and based upon the determined presence of CDH1 biallelic genetic inactivation, predicting that the patient has invasive lobular carcinoma. This prediction may further be based on certain received supplemental patient information (e.g., a family history of breast cancer).

The step 308 of predicting or diagnosing a disease may include predict a lobular phenotype and/or a CDH1 status using original and revised labels, following a histopathologic re-review of the histologic type and CDH1 status curation. For example, the step 308 of predicting or diagnosing a disease may include predicting a lobular phenotype and/or a CDH1 status, performing a histopathologic re-review of a histologic type and CDH1 status curation by incorporating information on biallelic CDH1 inactivation beyond CDH1 mutations, such as homozygous deletions, deleterious structural rearrangements, and loss-of-heterozygosity and gene promoter methylation, and, after performing the histopathologic re-review, repeating steps 306 and/or 308.

The method 300 may include outputting any of the detections, predictions, or diagnoses on an electronic display. For example, the method 300 may include a step 310 of outputting an indication of detected CDH1 biallelic genetic inactivation and/or CDH1 biallelic mutation. The method 300 may also include a step 312 of outputting a predicted or diagnosed disease (e.g., a type or subtype of cancer, such as BC or ILC). The outputs of steps 310 and/or 12 may be textual, numerical, statistical, visual (e.g., overlaid on one or more of the received digital images), and/or include audio.

In addition to predicting or diagnosing a disease, the method 300 may include predicting or determining a treatment plan and outputting the treatment plan. For example, the method 300 may predict a patient has ILC and determine a treatment plan that avoids, reduces, or minimizes chemotherapy and/or selective estrogen receptor modulators, and that includes and/or recommends surgery to remove abnormal cells and/or drugs to shrink and/or target abnormal cells.

Detection of ILCs by one or more above-described embodiments may be evaluated by experimental trials. For example, a convolutional neural network system to detect CDH1 biallelic genetic inactivation (AI-CDH1) using WSIs, as described above according to one or more embodiments, has been applied to data pertaining to 1,077 estrogen receptor positive (ER+) primary BCs with available MSK-IMPACT targeted sequencing data. Slides were reviewed by pathologists and slides with low tumor content or poor slide quality were excluded.

The example model was trained using a 10-fold cross-validation method to detect biallelic mutations, where the whole dataset was split into 10 folds with a ratio of 6:3:1 for train, tune, test sets, respectively. The mean number of positive and negative samples in the training set was 83.4 (SD=0.52) and 550.8 (SD=0.92) per fold, respectively. The example test set consisted of a mean of 13.90 (SD=0.32) positive and 91.80 (SD=0.42)) negative samples. The inference probabilities of both tune and test sets were computed. A universal optimal threshold may be determined from the inference probabilities of tune set samples by optimizing for F1 score. The optimal threshold may then be applied to each test set sample for converting the inference probability to binary predictions. The performance of the AI-CDH1 classifier may be evaluated to predict the lobular phenotype and CDH1 status, following a histopathologic re-review of the histologic type and CDH1 status curation. The latter may be conducted by incorporating information on biallelic CDH1 inactivation beyond CDH1 mutations (homozygous deletions, deleterious structural rearrangements, and loss-of-heterozygosity and gene promoter methylation).

In this example experiment, the AI-CDH1 classifier predicted biallelic CDH1 mutations with an area under the curve (AUC)=0.97 (95 CI: 0.93-1.00), sensitivity=82.73% and specificity=96.62%, PPV=78.77%, NPV=97.36% and accuracy=94.80%, and the 'lobular phenotype' with an AUC=0.974, sensitivity=87.72%, specificity=96.85%, PPV=87.72%, NPV=96.85% and accuracy=95%. Review of the CDH1 gene status revealed that BCs lacking CDH1 biallelic mutations harbored biallelic CDH1 inactivation by promoter methylation, homozygous deletions or structural rearrangements. Using the revised histologic re-classification and CDH1 biallelic inactivation status labels, the AI-CDH1 classifier may predict the lobular phenotype irrespective of CDH1 status (P>0.05).

Thus, by training a machine learning system to detect 'CDH1 biallelic mutations', as ground truth rather than histologic diagnosis of lobular carcinoma, which might be confounded by human subjectivity, an AI-based system according to one or more embodiments may detect ILCs accurately, thus providing a new paradigm for the development of AI-based cancer classification systems.

Figure 4:
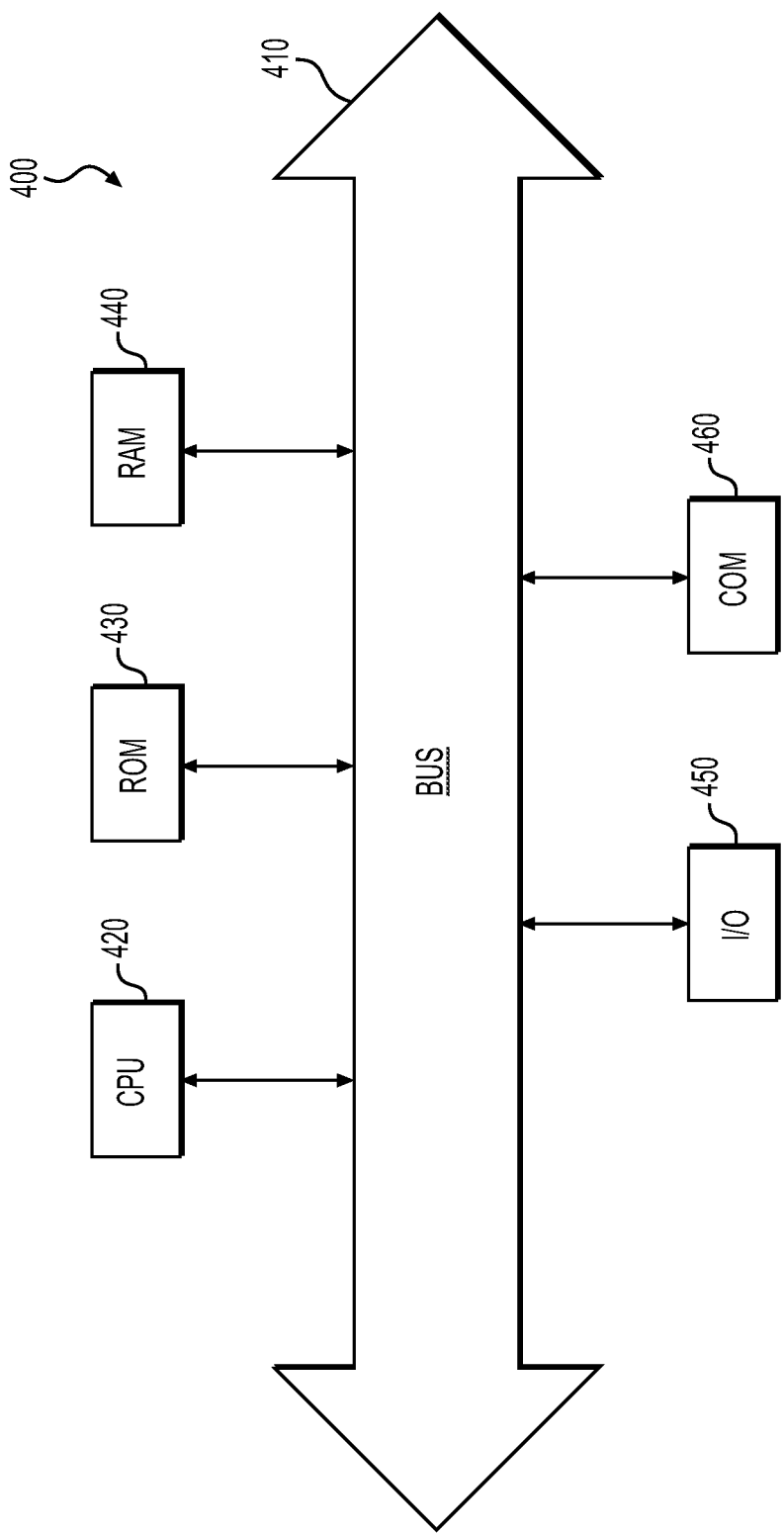
FIG. 4 depicts an example system that may execute techniques presented herein.

As shown in FIG. 4, a device 400 may include a central processing unit (CPU) 420. CPU 420 may be any type of processing device including, for example, any type of special purpose or a general-purpose microprocessor device. As will be appreciated by persons skilled in the relevant art, CPU 420 also may be a single processor in a multi-core/multiprocessor system, such system operating alone, or in a cluster of computing devices operating in a cluster or server farm. CPU 420 may be connected to a data communication infrastructure 410, for example a bus, message queue, network, or multi-core message-passing scheme.

Device 400 may also include a main memory 440, for example, random access memory (RAM), and may also include a secondary memory 430. Secondary memory 430, e.g., a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 430 may include similar means for allowing computer programs or other instructions to be loaded into device 400. Examples of such means may include a program cartridge and cartridge interface (such as that found in video game devices), a removable memory chip (such as an EPROM or PROM) and associated socket, and other removable storage units and interfaces, which allow software and data to be transferred from a removable storage unit to device 400.

Device 400 also may include a communications interface ("COM") 460. Communications interface 460 allows software and data to be transferred between device 400 and external devices. Communications interface 460 may include a model, a network interface (such as an Ethernet card), a communications, a PCMCIA slot and card, or the like. Software and data transferred via communications interface 460 may in the form of signals, which may be electronic, electromagnetic, optical or other signals capable of being received by communications interface 460. These signals may be provided to communications interface 460 via a communications path of device 400, which may be implemented using, for example, wire or cable, fiber optics, a phone line, a cellular phone link, an RF link or other communications channels.

The hardware elements, operating systems, and programming languages of such equipment are conventional in nature, and it is presumed that those skilled in the art are adequately familiar therewith. Device 400 may also include input and output ports 450 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically can be grouped together to perform a function or group of related functions. Like reference numerals are generally intended to refer to the same or similar components. Components and modules may be implemented in software, hardware or a combination of software and hardware.

The tools, modules, and functions described above may be performed by one or more processors. "Storage" type media may include any or all of the tangible memory of the computers, processors, or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments of the invention will be apparent to those skilled in the art from consideration of the specification and practice of the invention disclosed herein. It is intended that the specification and examples to be considered as exemplary only.

What is claimed is:

1. A computer-implemented method for diagnosing invasive lobular carcinoma, the method comprising:
   receiving one or more digital images into a digital storage device, the one or more digital images including images of breast tissue of a patient;
   applying a trained machine learning module to detect a presence or absence of CDH1 biallelic genetic inactivation and/or CDH1 biallelic mutation from the received one or more digital images, the trained machine learning module having been trained using labels of one or more training digital images, wherein the labels correspond to a presence or absence of CDH1; and
   determining whether the patient has invasive lobular carcinoma using the detected presence or absence of the CDH1 biallelic genetic inactivation and/or CDH1 biallelic mutation as ground truth, the trained machine learning module having been trained using a plurality of digital images of breast tissue from a plurality of patients and associated mutation data, the associated mutation data comprising integrated mutation profiling of actionable cancer targets (MSK-IMPACT) targeted sequencing data.

2. The computer-implemented method of claim 1, wherein the trained machine learning module was trained using a 10-fold cross-validation method.

3. The computer-implemented method of claim 1, further including applying the trained machine learning module to predict a lobular phenotype.

4. The computer-implemented method of claim 1, further comprising:
   receiving supplemental patient information, wherein determining whether the patient has invasive lobular carcinoma is based on the received supplemental patient information.

5. The computer-implemented method of claim 4, wherein the supplemental patient information includes patient demographics, medical history, cancer treatment history, family history, past biopsy or cytology information, additional test results, radiology imaging, genomic test results, molecular test results, historical pathology specimen images, and/or location of the breast tissue.

6. The computer-implemented method of claim 1, further comprising outputting the determination on an electronic display.

7. A system for diagnosing invasive lobular carcinoma, comprising:
   at least one memory storing instructions; and
   at least one processor configured to execute the instructions to perform operations comprising:
      receiving one or more digital images into a digital storage device, the one or more digital images including images of breast tissue of a patient;
      applying a trained machine learning module to detect a presence or absence of CDH1 biallelic genetic inactivation and/or CDH1 biallelic mutation from the received one or more digital images, the trained machine learning module having been trained using labels of one or more training digital images, wherein the labels correspond to a presence or absence of CDH1; and
      determining whether the patient has invasive lobular carcinoma using the detected presence or absence of the CDH1 biallelic genetic inactivation and/or CDH1 biallelic mutation as ground truth, the trained machine learning module having been trained using a plurality of digital images of breast tissue from a plurality of patients and associated mutation data, the associated mutation data comprising integrated mutation profiling of actionable cancer targets (MSK-IMPACT) targeted sequencing data.

8. The system of claim 7, wherein the trained machine learning module was trained using a 10-fold cross-validation method.

9. The system of claim 7, wherein the operations further comprise applying the trained machine learning module to predict a lobular phenotype.

10. The system of claim 7, wherein the operations further comprise:
    receiving supplemental patient information, wherein determining whether the patient has invasive lobular carcinoma is based on the received supplemental patient information.

11. The system of claim 10, wherein the supplemental patient information includes patient demographics, medical history, cancer treatment history, family history, past biopsy or cytology information, additional test results, radiology imaging, genomic test results, molecular test results, historical pathology specimen images, and/or location of the breast tissue.

12. The system of claim 7, wherein the operations further comprise outputting the determination on an electronic display.

13. A non-transitory computer-readable medium storing instructions that, when executed by a processor, cause the processor to perform operations for diagnosing invasive lobular carcinoma, the operations comprising:
    receiving one or more digital images into a digital storage device, the one or more digital images including images of breast tissue of a patient;
    applying a trained machine learning module to detect a presence or absence of CDH1 biallelic genetic inactivation and/or CDH1 biallelic mutation from the received one or more digital images, the trained machine learning module having been trained using labels of one or more training digital images, wherein the labels correspond to a presence or absence of CDH1; and
    determining whether the patient has invasive lobular carcinoma using the detected presence or absence of the CDH1 biallelic genetic inactivation and/or CDH1 biallelic mutation as ground truth, the trained machine learning module having been trained using a plurality of digital images of breast tissue from a plurality of patients and associated mutation data, the associated mutation data comprising integrated mutation profiling of actionable cancer targets (MSK-IMPACT) targeted sequencing data.

14. The computer-readable medium of claim 13, wherein the operations further comprise receiving supplemental patient information, wherein determining whether the patient has invasive lobular carcinoma is based on the received supplemental patient information.

\* \* \* \* \*